(12) United States Patent
Sato et al.

(10) Patent No.: US 12,279,634 B2
(45) Date of Patent: Apr. 22, 2025

(54) LIQUID FOOD COMPOSITION COMPRISING PEA OR FAVA BEAN PROTEINS AND IMPROVED MINERAL PROFILE FOR NUTRITION

(71) Applicant: ROQUETTE FRERES, Lestrem (FR)

(72) Inventors: Ayana Sato, Chiba (JP); Aiwei Peng, Singapour (SG); Goichi Ito, Tokyo (JP); Sayaka Hori, Tokyo (JP)

(73) Assignee: Roquette Freres, Lestrem (FR)

( * ) Notice: Subject to any disclaimer, the term of this patent is extended or adjusted under 35 U.S.C. 154(b) by 365 days.

(21) Appl. No.: 17/756,540

(22) PCT Filed: Nov. 26, 2020

(86) PCT No.: PCT/EP2020/083515
§ 371 (c)(1),
(2) Date: May 26, 2022

(87) PCT Pub. No.: WO2021/105287
PCT Pub. Date: Jun. 3, 2021

(65) Prior Publication Data
US 2022/0408760 A1    Dec. 29, 2022

(30) Foreign Application Priority Data
Nov. 26, 2019   (EP) .................................. 19306526

(51) Int. Cl.
*A23C 19/09*   (2006.01)
*A23B 2/40*    (2025.01)
(Continued)

(52) U.S. Cl.
CPC ................ *A23L 2/66* (2013.01); *A23B 2/40* (2025.01); *A23J 3/14* (2013.01); *A23L 33/16* (2016.08);
(Continued)

(58) Field of Classification Search
CPC .......... A23L 2/66; A23L 33/16; A23L 33/185; A23L 3/16; A23J 3/14; A23V 2002/00
(Continued)

(56) References Cited

U.S. PATENT DOCUMENTS

2019/0021387 A1    1/2019  Barata et al.
2019/0216126 A1    7/2019  Foster et al.

FOREIGN PATENT DOCUMENTS

CN         108719977 A      11/2018
WO    WO-2012027287 A1 *  3/2012 ............. A23L 1/296
(Continued)

OTHER PUBLICATIONS

Database GNPD [Online] MINTEL; Apr. 24, 2018 (Apr. 24, 2018), anonymous, "Strawberry Flavoured Recovery 3:1 Post Exercise Drink", XP055688956, retrieved from www.gnpd.com Database accession No. 5618031; the whole document.
(Continued)

*Primary Examiner* — Brent T O'Hern

(57) ABSTRACT

The present invention relates to a liquid food composition, in particular a beverage, based on pea and/or fava bean proteins, having an improved mineral composition, in order to fit with human nutrition requirements and characterized in that it includes tricalcium phosphate and magnesium carbonate as only divalent salts. The invention also pertains to a process for obtaining said liquid composition, and also to the uses thereof, in particular in the food-processing field and most particularly the preparation of food formulations and specialized nutrition.

21 Claims, 1 Drawing Sheet

Photos of liquid composition

1a) No minerals / No heat

1b) No minerals / After heat treatment

1c) Minerals / No heat

1d) Minerals / After heat treatment

(51) Int. Cl.
  *A23J 3/14* (2006.01)
  *A23L 2/66* (2006.01)
  *A23L 33/16* (2016.01)
  *A23L 33/185* (2016.01)

(52) U.S. Cl.
  CPC ......... *A23L 33/185* (2016.08); *A23V 2002/00* (2013.01)

(58) Field of Classification Search
  USPC .......................................................... 426/74
  See application file for complete search history.

(56) References Cited

FOREIGN PATENT DOCUMENTS

| WO | 2014068226 A1 | 5/2014 |
|---|---|---|
| WO | 2016/049018 A1 | 3/2016 |
| WO | 2017/059101 A1 | 4/2017 |
| WO | 2019/068999 A1 | 4/2019 |
| WO | 2020/193641 A1 | 10/2020 |
| WO | 2020/193668 A1 | 10/2020 |

OTHER PUBLICATIONS

Database GNPD [Online] MINTEL; Jul. 12, 2018 (Jul. 12, 2018), anonymous, "Mixed Nuts Drink", XP055688963, retrieved from www.gnpd.com Database accession No. 5813211; whole document.

Database GNPD [Online] MINTEL; Jul. 24, 2017 (Jul. 24, 2017), anonymous "Veg Protein Booster", XP055688964, retrieved from www.gnpd.com Database accession No. 4953217; the whole document.

Database GNPD [Online] MINTEL; "Food for Special Medical Purposes," retrieved from www.gnpd.com, database accession No. 367657, 2016. (The English abstract included.).

Database GNPD [Online] MINTEL; "Coconut and Chocolate Flavoured Shake," retrieved from www.gnpd.com, database accession No. ID 4850057, 2017. (The English abstract included.).

\* cited by examiner

Photos of liquid composition
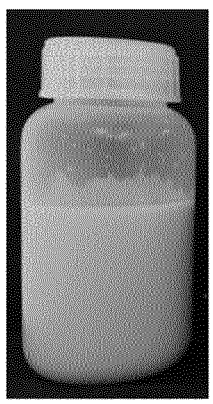
1a) No minerals / No heat
1b) No minerals / After heat treatment
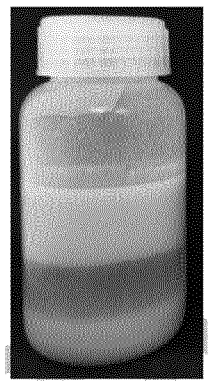
1c) Minerals / No heat
1d) Minerals / After heat treatment

LIQUID FOOD COMPOSITION COMPRISING PEA OR FAVA BEAN PROTEINS AND IMPROVED MINERAL PROFILE FOR NUTRITION

CROSS-REFERENCE TO RELATED APPLICATIONS

This application is a National Stage Application of PCT/EP2020/083515 filed Nov. 26, 2020, which claims priority from European Patent Application No. 19306526.5 filed on Nov. 26, 2019. The priority of said PCT and European Patent Application are claimed. Each of the prior mentioned applications is hereby incorporated by reference herein in its entirety.

FIELD OF THE INVENTION

The present invention relates to a liquid food composition, in particular a beverage, based on pea or fava bean protein, having an improved mineral composition, in order to fit with human nutrition requirements. The invention also pertains to a process in order to obtain said liquid composition, and also to the uses thereof, in particular in the food-processing field and most particularly the preparation of food formulations and specialized nutrition.

PRIOR ART

Along with carbohydrates and lipids, proteins constitute a significant part of our diet. Daily protein requirements are generally between 12% and 20% of food intake.

Generally, consumed proteins are either of animal origin (referred to as animal proteins), for instance meat, fish, eggs and milk products, or of plant origin (referred to as plant proteins), for instance cereals, oleaginous plants and leguminous plants.

In industrialized countries, protein intakes are mainly in the form of animal proteins. However, many studies demonstrate that excessive consumption of animal proteins to the detriment of plant proteins is one of the causes of increase of cancer and cardiovascular diseases.

Moreover, animal proteins have many disadvantages, both in terms of their allergenicity, in particular proteins from milk or eggs, and environmental impact, in particular the damaging effects of intensive farming.

Thus, as an alternative, manufacturers have gradually turned to plant proteins. Indeed, it is known practice to use plant proteins in order to replace all or some of the animal proteins in foods.

Such a replacement is not always easy because plant proteins have functional properties that are different from those of animal proteins. These functional properties can be physical or physicochemical properties which have an effect on the sensory qualities of food compositions generated during technological transformations, storage or domestic culinary preparations.

One drawback of certain plant proteins, in particular pea proteins, is that they don't behave like milk proteins, particularly in terms of texture when formulated. This drawback is especially challenging in the formulation of liquid formulation, especially beverages.

Liquid compositions are often difficult to formulate, especially with high level of minerals, as they will further exhibit coagulation. In this field, divalent salts are particularly known to trigger pea protein coagulation. For instance, in WO2014068226 filed by present applicant, calcium ions are used to lower pea protein solubility.

Coagulation of pea proteins will change texture of liquid formulation. Such texture change will result in many problems ranging from liquid stability under storage, with the need for the customer to shake the beverage before consumption, to organoleptic issues like sandy mouthfeel apparition, which is a serious obstacle for consumers to accept premium vegetal-based powder beverages.

Similar problems have been also observed by the applicant for liquid formulations comprising minerals based on fava bean proteins.

A common solution to this problem consists in formulating the beverage with hydrocolloids in order to stabilize proteins. For instance, "*Comparative studies on the stabilization of pea protein dispersions by using various polysaccharides*" (Wei & al., Food Hydrocolloids, 98, 2020) presents various polysaccharides that help to stabilize pea proteins in liquid formulation. However, the addition of such hydrocolloids can refrain some customers who seek food products that possess the less possible compounds on its label.

The issue of stability is more limited in powder mixes to manufacture liquid food compositions whether food should be ingested immediately after blending, However, the issue may still even though remain, especially if the liquid food product is stored between preparation and consumption.

Such powder mixes comprising minerals have already been described, for example in WO 2012/027287 A1 which describes the use of pea protein hydrolysates in infant formula nutritional powders comprising different minerals. For each of these minerals, no specific effect is described regarding coagulation, stabilization and texture.

The document WO2016/049018 A1 describes a fatty acid composition for making fatty acid fortified nutritional products; the fatty acid composition being in powder form and comprising: a fatty acid component, optionally at least one vitamin, optionally inorganic salts, an optional protein source, and an optional carbohydrate source. If the pea protein isolate is one of the different listed optional protein sources, none of the powder fatty acids compositions of the examples comprise such a protein.

CN108719977 describes a breast cancer nutritional food comprising different ingredients including magnesium and calcium salts and a protein material selected from pea protein and whey protein, or pea peptide and whey protein. For each of these minerals, no specific effect is described regarding coagulation, stabilization and texture of the obtained food. Other liquid food products existing on the market are also nut milks enriched in proteins and minerals. Perhaps the most prominent challenge for those trying to produce good quality non-dairy beverages is product stabilisation. Due to the types of fat (with low saturation to deliver on nutritional claims) often used in such drinks, the emulsion is, by nature, very sensitive, with sedimentation, flocculation and fat separation as constant issues.

Thus, in order to promote the replacement of animal proteins by plant proteins in the food processing industry, there is still a need for a solution which makes it possible to allow improved mineral formulation of pea protein-based liquid food compositions, while avoiding pea protein coagulation, and without adding other compounds in order to stabilize liquid formulation.

The Applicant has thus, to its credit, developed such a composition and its manufacturing process, which will be disclosed in more details below.

SUMMARY OF THE INVENTION

A first object of the present invention is a liquid food composition comprising protein and minerals sources characterized in that the source of protein is from pea and/or fava bean and the source of minerals comprises magnesium carbonate and tricalcium phosphate.

None of the prior arts cited above describe a liquid food composition combining magnesium carbonate with tricalcium phosphate.

The liquid food composition of the invention exhibits improved organoleptic & textured properties, in particular no coagulation, and improved mineral profile without the need to add hydrocolloids.

A second object of the present invention is a process for preparing the liquid food composition of the invention, said process comprising mixing pea and/or fava bean proteins with magnesium carbonate and tricalcium phosphate.

BRIEF DESCRIPTION OF THE SEVERAL VIEWS OF THE DRAWING

FIG. 1 shows how minerals and heat treatment (sterilization, HTST, etc.) can lead to coagulation of a recipe.

DETAILED DESCRIPTION OF THE INVENTION

A first object of the present invention is a liquid food composition comprising protein and minerals sources characterized in that source of protein is from pea and/or fava bean and the source of minerals comprises magnesium carbonate and tricalcium phosphate.

For the purposes of the present invention, "liquid" describe a substance that flows freely but is of constant volume, having a consistency like that of water or oil.

In a preferred embodiment, the liquid food composition of the invention can be produced, stored and used in a liquid state. In a less preferred embodiment, liquid food composition may be dried and rehydrated, i.e. by addition of water, before being consumed. In this case, the drying step needs to be carefully handled in order not to coagulate pea protein.

For the purposes of the present invention, "food composition" is intended to mean a composition that can be ingested by an animal or a human being. Examples of food compositions include foodstuffs for human consumption, animal feed and beverages.

For the purposes of the present invention, "organoleptic properties" is intended to mean aspects of a composition that a person experiences via the senses-including taste, sight, smell, and touch.

Proteins introduced in the composition of the invention are pea and/or fava bean proteins, derived from a pea and/or fava plant seeds, for example by extraction and optionally further modification.

The term "pea" is herein considered in its broadest accepted sense and includes in particular:
all varieties of "smooth pea" and of "wrinkled pea", and all mutant varieties of "smooth pea" and of "wrinkled pea", this being whatever the uses for which said varieties are generally intended (food for human consumption, animal feed and/or other uses).

In the present application, the term "pea" includes the varieties of pea belonging to the *Pisum* genus and more particularly *Pisum sativum*.

Said mutant varieties are in particular those known as "r mutants", "rb mutants", "rug 3 mutants", "rug 4 mutants", "rug 5 mutants" and "lam mutants" as described in the article by C-L HEYDLEY et al. entitled "Developing novel pea starches", Proceedings of the Symposium of the Industrial Biochemistry and Biotechnology Group of the Biochemical Society, 1996, pp. 77-87.

In a preferred embodiment, said pea protein is derived from smooth pea.

Peas are leguminous plants with protein-rich seeds which have been the widely developed in Europe and in France since the 1970s, not only as a protein source for animal feed, but also as food for human consumption.

Fava bean is understood to mean the group of annual plants of the species *Vicia faba*, belonging to the group of leguminous plants of the Fabaceae family, the Faboideae subfamily and the Fabeae tribe. The varieties Minor and Major can be distinguished. Wild varieties and those obtained by genetic engineering or varietal selection are all excellent sources.

Like all leguminous-plant proteins, pea and fava bean proteins consist of three main classes of proteins: globulins, albumins and "insoluble" proteins. In a preferred embodiment, the protein is selected from pea or fava bean globulins. Different pea globulins are commercialized by the applicant and can be for example NUTRALYS® S85F. Different fava bean globulins have been described by the Applicant in the patent applications WO2020/193668 and WO2020/193641.

Preferably, globulin proteins present a degree of hydrolysis (DH) below 10%, for example below 5%. This measurement can be based on the method for determining the amino nitrogen on proteins and protein isolates according to the invention with the MEGAZYME kit (reference K-PANOPA) and calculation of the degree of hydrolysis. A detailed method is described in document US20190021387 A1.

Generally, the liquid food compositions of the invention comprise, based on the total content of protein, at least 50% by weight of pea and/or fava bean proteins.

In an embodiment, the liquid composition is characterized in that the source of protein consists of at least 60% of pea globulin and/or fava bean globulins and at most 40% of another source of protein, preferably cereal proteins and/or pea albumin. For example, the pea and/or fava bean globulin and the other source of protein can be present in a ratio going from 65/35 to 85/15, preferably from 70/30 to 82/18, more preferably from 75/25 to 80/20. In these embodiments, the protein can present a good Protein Digestibility Corrected Amino Acid Score (PDCAAS).

The other source of protein can be milk protein, such as whey or casein, pea and fava bean albumin or cereal protein, such as rice and/or wheat protein. Preferably, the other source of protein is cereal protein. In an embodiment, the liquid food composition is almost free of soy protein, i.e. comprises less than 5% of soy protein based on the total solid content of the liquid food composition, preferably free of soy protein. In an embodiment, the liquid food compositions is almost free of leguminous protein other than pea and fava bean, i.e. comprise less than 5% of leguminous protein other than pea and fava bean based on the total solid content of the liquid food composition, preferably free of leguminous protein other than pea and fava bean.

In another alternative embodiment, the pea protein consists of a more than 75% of pea globulin and less than 25% of another source of protein, preferably in order to reach PDCAAS of 1.

In these particular embodiments it is seeked to increase the PDCAAS, for example to reach a PDCAAS above 0,97, for example of 1, in order to provide the right amount of essential aminoacids. Such a protein solution combining pea globulin and pea albumin can be for instance found in WO2019/068999 owned by applicant. To produce fava bean globulin and/or albumin, the same process disclosed in patent application WO2019/068999 can be conducted, except that the starting material (pea flour) is replaced by fava bean flour.

PDCAAS can be determined by the methods known by the man skilled in the art, using as a reference: "Protein Quality Evaluation. Report of a Joint FAO/WHO Expert Consultation, 2008".

The value of pea proteins lies in their good emulsifying capacities, their lack of allergenicity and their low cost, which makes them an economical functional ingredient.

Furthermore, pea proteins favourably contribute to sustainable development and their carbon impact is very positive. This is because pea cultivation is environmentally friendly and does not require nitrogenous fertilizers, since the pea fixes atmospheric nitrogen.

In another embodiment, the source of protein consists of a more than 75% of pea globulin and less than 25% of another source of protein in order to reach a PDCAAS of 1. Suitable sources of non-pea globulin protein comprise rice proteins or wheat proteins.

The liquid compositions of interest are mainly beverages. Such beverages may be chosen from the group consisting of:
  beverages intended for dietetic nutrition,
  beverages intended for the nutrition of sportsmen and sportswomen,
  beverages intended for infant nutrition,
  beverages intended for clinical nutrition and/or for individuals suffering from undernourishment,
  beverages intended for the nutrition of the elderly.

Liquid compositions can also be for other food application than beverages such as solutions for enteral nutrition.

As used herein, the term "source of mineral" refers to an inorganic salt of calcium or magnesium. Such divalent ions are desirable in liquid food formulations because of their nutritional value. However, it is generally considered that such soluble salts of divalent ions, when they are dissolved in aqueous solutions, interact with the proteins present in such solutions and make them coagulate.

The inventors have surprisingly shown that magnesium carbonate is a suitable source of magnesium and that tricalcium phosphate is a suitable source of calcium for liquid food formulations comprising pea and/or fava proteins.

In a preferred embodiment of the invention, the mineral source of the liquid food composition of the invention consists in magnesium carbonate and tricalcium phosphate.

As used herein, the term "magnesium carbonate" refers to an inorganic salt whose chemical formula is $MgCO_3$. Several hydrated and basic forms of magnesium carbonate also exist as minerals. he most common magnesium carbonate forms are the anhydrous salt called magnesite ($MgCO_3$) and the di, tri, and pentahydrates known as barringtonite ($MgCO_3 \cdot 2\ H_2O$), nesquehonite ($MgCO_3 \cdot 3\ H_2O$), and lansfordite ($MgCO_3 \cdot 5\ H_2O$), respectively. Some basic forms such as artinite ($MgCO_3 \cdot Mg(OH)_2 \cdot 3\ H_2O$), hydromagnesite (4 $MgCO_3 \cdot Mg(OH)_2 \cdot 4\ H_2O$), and dypingite (4 $MgCO_3 \cdot Mg(OH)_2 \cdot 5\ H_2O$) also occur as minerals.

Magnesite consists of white trigonal crystals. The anhydrous salt is practically insoluble in water, acetone, and ammonia. All forms of magnesium carbonate react in acids. Magnesium carbonate crystallizes in the calcite structure where in $Mg^{2+}$ is surrounded by six oxygen atoms. The dihydrate one has a triclinic structure, while the trihydrate has a monoclinic structure. References to 'light' and 'heavy' magnesium carbonates actually refer to the magnesium hydroxy carbonates hydromagnesite and dypingite (respectively).

As used herein, the term "tricalcium phosphate" refers to a calcium salt of phosphoric acid with the chemical formula $Ca_3(PO_4)_2$. It is also known as tribasic calcium phosphate and bone phosphate of lime (BPL). It is a white solid of low solubility. Most commercial samples of "tricalcium phosphate" are in fact hydroxyapatite. It exists as three crystalline polymorphs $\alpha$, $\alpha'$, and $\beta$. The $\alpha$ and $\alpha'$ states are stable at high temperatures.

In a preferred embodiment, the amount of magnesium carbonate in the composition may be from 0.15% to 0.35% preferably from 0.20% to 0.30%, more preferably around 0.25%, by weight based on the dry weight of the composition.

In a preferred embodiment, the amount of tricalcium phosphate in the composition may be from 0.4 to 1.2%, advantageously from 0.8% to 1.2% preferably from 0.9% to 1.1%, more preferably around 1%, by weight based on the dry weight of the composition.

In a preferred embodiment, the liquid composition also comprises a potassium source, preferably selected in the list consisting of potassium pyrophosphate, potassium tripolyphosphate and potassium metaphosphate. The stability of the liquid food composition is even higher when selecting one of the three potassium salts of this list, compared to a liquid food composition comprising another potassium salt.

In such embodiment, the amount of potassium pyrophosphate in the composition will be advantageously from 0.7 to 2%, preferably from 1% to 2%, more preferably from 1.25% to 1.75%, more preferably around 1.5%, by weight based on the dry weight of the composition; the amount of potassium tripolyphosphate in the composition may be from 0.7% to 2%, advantageously 1% to 2% preferably from 1.25% to 1.75%, more preferably around 1.5%, by weight based on the dry weight of the composition; and the amount of potassium metaphosphate in the composition may be from 1.0% to 2.5%, advantageously from 1.5% to 2.5%, preferably from 1.75% to 2.25%, more preferably around 2%, by weight based on the dry weight of the composition.

An embodiment of the invention concerns a liquid food composition wherein the amount of magnesium carbonate in the composition is from 0.15% to 0.35% by weight based on the dry weight of the composition, the amount of tricalcium phosphate in the composition is from 0.4% to 1.0% and the amount of potassium pyrophosphate in the composition is from 0.7% to 1.2% by weight based on the dry weight of the composition, the amount of potassium tripolyphosphate in the composition is from 0.7% to 1.2% by weight based on the dry weight of the composition; and/or the amount of potassium metaphosphate in the composition is from 1% to 1.5% by weight based on the dry weight of the composition.

According to the invention, when the mineral source of a given element comprises a specific mineral salt, it comprises preferably at least 90% by weight of this specific mineral salt based on the total minerals salts comprising this element in the composition, more preferably the mineral source of this element essentially consists of this specific mineral salt. For example, if the calcium source comprises tricalcium phosphate, it preferably comprises at least 90% by weight of tricalcium phosphate based on the total calcium mineral salts added in the composition, more preferably the calcium source essentially consists of tricalcium phosphate.

The liquid food compositions are generally almost free of grinded nuts, i.e. comprise less than 5% of grinded nuts based on the total solid content of the liquid food composition. Preferably, the liquid food compositions are free of grinded nuts. Exemplary nuts include almond, chestnut, pecan, hazelnut, cashew, pine nut, brazil nut and walnut.

Unless explicitly stated otherwise, the contents of each component of the liquid composition are expressed in dry relative contents of the total dry solids content of the liquid food composition. Each component can comprise some impurities.

All embodiments above can be characterized by a Zeta potential below −30 mV, preferably comprised between −35 mV and −45 mV.

In this application "Zeta potential" must be understood as electrokinetic potential in colloidal dispersions. In the colloidal chemistry literature, it is usually denoted using the Greek letter zeta (ζ), hence ζpotential. The usual units are volts (V) or millivolts (mV). From a theoretical viewpoint, the zeta potential is the electric potential in the interfacial double layer at the location of the slipping plane relative to a point in the bulk fluid away from the interface. In other words, zeta potential is the potential difference between the dispersion medium and the stationary layer of fluid attached to the dispersed particle.

The zeta potential is caused by the net electrical charge contained within the region bounded by the slipping plane, and also depends on the location of that plane. Thus, it is widely used for quantification of the magnitude of the charge.

The zeta potential is a key indicator of the stability of colloidal dispersions. The magnitude of the zeta potential indicates the degree of electrostatic repulsion between adjacent, similarly charged particles in a dispersion. For molecules and particles that are small enough, a high zeta potential will confer stability, i.e., the solution or dispersion will resist aggregation. When the potential is small, attractive forces may exceed this repulsion and the dispersion may break and flocculate. So, colloids with high absolute values of zeta potential (negative or positive) are electrically stabilized while colloids with low zeta potentials tend to coagulate or flocculate as outlined in the table below:

| Zeta potential (mV) | Stability behavior |
| --- | --- |
| 0 to ±5 | Rapid coagulation or flocculation |
| ±10 to ±30 | Incipient instability |
| ±30 to ±40 | Moderate stability |
| ±40 to ±60 | Good stability |
| >61 | Excellent stability |

The present invention also encompasses the process for preparing the liquid food composition as defined above, said process comprising mixing pea and/or fava bean proteins, with magnesium carbonate and tricalcium phosphate.

Said process can be carried out according to the common practices of those skilled in the art. For example, the process can comprise mixing, on the one hand, an aqueous solution or suspension comprising pea proteins and/or fava bean with, on the other hand, an aqueous solution comprising magnesium carbonate and tricalcium phosphate. As described above, pea and/or fava bean proteins can also be with other source of proteins in order to rectify PDCAAS to 1, for example less than 25% of other protein. Lastly, as described above, magnesium carbonate and tricalcium phosphate can also be additioned with potassium salts selected in the list consisting of potassium pyrophosphate, potassium tripolyphosphate and potassium metaphosphate.

In certain embodiments, the solution may further be homogenized, heat sterilized and dried. In particular, the homogenization may be carried out at high pressure. Any pressure can be applied as long at the end of the homogenization the liquid food composition presents a particle size smaller than before the homogenization step. For example, it can be at a pressure of between 2 MPa and 800 MPa, for example between 2 MPa and 250 MPa, for example between 3 MPa and 100 MPa, in particular between 15 MPa and 50 MPa, and most particularly at approximately 20 MPa.

The homogenized or non-homogenized aqueous solution or suspension may be subjected to a heat-sterilization step.

In general, heat sterilization can be carried out by heating the composition, for example at a temperature greater than 100° C., for a period of time sufficient to inhibit the enzymes and any form of microorganisms, in particular sporulating bacteria. The sterilization may be carried out at high temperature, that is to say a temperature of 135° C. to 150° C., for a period usually not exceeding 15 seconds, which corresponds to UHT (Ultra-High Temperature) sterilization. This technique has the advantage of preserving the nutritional and organoleptic properties of the sterilized product.

The heat-sterilization step can be carried out by means of the devices and techniques known to those skilled in the art. The heat-sterilized aqueous solution may be further subjected to drying which can be done by well-known technology like spray-drying.

In another embodiment, the process can comprise mixing directly pea and/or fava proteins and magnesium carbonate and tricalcium phosphate. The dry mixing can be done using well-known apparatus from the state of the art. In this case, the dry powder composition of the invention can be directly packed and sold.

The mixing step may be advantageously carried out in such a way as to obtain a composition with the previously defined weight percentages of magnesium carbonate and tricalcium phosphate based on the dry weight of the composition.

In a preferred embodiment, the process of the invention may further comprise the addition of one or more nutritional additives to said composition.

In a preferred embodiment of the invention, the liquid food composition does not comprise any hydrocolloid or thickener additive. It is a key advantage of the invention that no hydrocolloids or thickener additives are added in order to stabilize coagulation of proteins due to mineral composition. Additives are only added in order to change flavor, change color, add nutritional advantage.

The additive(s) can in particular be chosen from soluble fibers, sugar, vegetable oils, emulsifying agents, food dyes, preservatives or sweeteners.

Preferably, the soluble plant fibre is chosen from the group consisting of fructans including fructooligosaccharides (FOSs) and inulin, glucooligosaccharides (GOSs), isomaltooligosaccharides (IMOs), trans-galactooligosaccharides (TOSs), pyrodextrins, polydextrose, branched maltodextrins, indigestible dextrins and soluble oligosaccharides derived from oleaginous or protein-producing plants.

The term "soluble fibre" is intended to mean water-soluble fibres. The fibres can be quantitatively determined according to various AOAC methods. Mention may be made, by way of example, of AOAC methods 997.08 and 999.03 for fructans, FOSs and inulin, AOAC method 2000.11 for polydextrose, AOAC method 2001.03 for quantitatively determining the fibres contained in branched maltodextrins and indigestible dextrins, or AOAC method 2001.02 for GOSs and also soluble oligosaccharides derived from oleaginous or protein-producing plants.

Advantageously, the soluble plant fibre is obtained from partially hydrolysed wheat or corn starch, and contains up to 85% of total fibre.

Sugar can include saccharose, glucose, fructose or any composition comprising these, such as glucose syrups, glucose-fructose syrups, or maltodextrins.

Preferably, the vegetable oil is chosen from groundnut, avocado, borage, camelina, safflower, hemp, rapeseed, wheat germ, linseed, nigella, hazelnut, walnut, olive, evening primrose, marrow seed, grapeseed, perilla, sesame, soya bean and sunflower oils. Preferably, the vegetable oil rapeseed and/or soya bean oil.

Preferably, the emulsifying agent is chosen from lecithin, sucrose esters, fatty acid mono- and diglycerides, and sorbitan esters. Preferably, the emulsifying agent is chosen from fatty acid monoglycerides. In a preferred embodiment, the emulsifying agent comprises diacetyl tartarcic acid esters of monoglyceride (DATEM) and/or succinic acid esters of monoglyceride) (POEM B-30).

The invention will be understood more clearly on reading the examples which follow, which are intended to be purely illustrative and do not in any way limit the scope of the protection.

EXAMPLES

List of the ingredients used:
NUTRALYS® S85F, Roquette Frères (France) (which comprises 85% pea protein)
Pea protein isolate, Shuangta (China)
Soy protein isolate, Nisshin-oillio (Japan)
The various salts are bought from chemical products suppliers like Sigma Aldrich. List of additives used are:
GLUCIDEX® 19 (maltodextrins) from ROQUETTE (France)
NUTRIOSER FB06 (soluble fiber) from ROQUETTE (France)
Rapeseed and Soybean oil from Nishin-oillio and J-oil
RD-2010 (vitamin) from DSM (Netherlands)
DATEM (diacetyl tartaric acid esters of monoglyceride) and POEM B-30 (Succinic acid esters of monoglyceride) from Riken-vitamin Recipe of beverage is summarized in Table 1 below (quantities are indicated in g):

| | |
|---|---|
| Protein | 50 |
| Glucidex ® 19 | 130 |
| Saccharose | 35 |
| Nutriose ® FB06 | 20 |
| Rapeseed oil | 14 |
| Soy bean oil | 14 |
| Demineralized water | 550 |
| DSM Vitamin RD-2010 | 0.2 |
| DATEM[diacetyl tartaric acid esters of monoglyceride] | 0.8 |
| POEM B-30[Succinic acid esters of monoglyceride] | 0.8 |
| Different salts to check impact on final product | Quantity depending on nutritional requirement in grams (an approximate dry content, based on dry solids of the composition (% dsb) is also calculated for facilitation purposes) |

Process to obtain beverage is described below:
1. Mix all powders except emulsifiers
2. Mix rapeseed & soybean oils with emulsifiers (DATEM and POEM B-30). Heat up to 60° C. to melt.
3. Mix demineralized water heated at 60° C. and powder mix with homomixer at 6000 rpm for 30 sec to melt well.
4. Add oil mix into the liquid while mixing at 6000 rpm for 15 sec. And then mix for extra 1 min.
5. Homogenize the liquid at 15 MPa twice.
6. Adjust pH at 7,0 with lactic acid
7. Pour 200 g of sample into a bottle.
8. Sterilize at 121° C. for 10 min by autoclave. Put 6 bottles in one autoclave batch.
9. After completing the autoclave process, cool the samples with ice water for 15 min.
10. Keep samples in refrigerator, 4° C., for 1 night.

The liquid nutritional beverage obtained has the following characteristics:

| | per 125 ml | per 100 kcal |
|---|---|---|
| Energy | 200 [kcal] | 100 [kcal] |
| Protein | 7.5 [g] | 3.75 [g] |
| Fat | 5.6 [g] | 2.82 [g] |
| Carbohydrate | 31.7 [g] | 15.85 [g] |
| Fiber | 2.5 [g] | 1.25 [g] |

Analysis to check the quality of final products are:
Visual observation (0=homogenous liquid without coagulates/1=non homogenous liquid with aggregates that sediments)
Zeta potential and particle size with Zetasizer Nano ZS from Malvern (Pattern: 1.45+0.001i, Dispersan=water, Model: Smoluchowski F(ka)=1.5, Temperature: 25° C., Cells: DTS 1070, Measurement duration: Automatic and Number of measurement: 3)
Viscosity with TA Discovery HR Hybrid Rheometer (Geometry: concentric cylinder, Temperature: 20° C., Equilibrium time: 3 min, Shear rate: from 0.6 to 300 $s^{-1}$, Dynamic viscosity measured at 5 and 40 $s^{-1}$)
Sedimentation (quantity settled after centrifugation at 4000 G for 40 min)

A control recipe without salts is done in triplicate as a goal:

| | Visual observation | Sedimentation (%) | Zeta potential (mV) | Viscosity 5 s−1 | Viscosity 40 s−1 |
|---|---|---|---|---|---|
| Control Recipe #1 | 0 | 0 | −42.37 | 107 | 67 |
| Control Recipe #2 | 0 | 1.5 | −38.87 | 111 | 74 |
| Control Recipe #3 | 0 | 0 | −39.03 | 104 | 68 |

Example 1: Effect of Various Calcium and Magnesium Salt Addition

As indicated above, each calcium salt was incorporated in the liquid food composition in order to obtain the same quantity of calcium cation.

|  | Visual observation | Salt quantity (g) | Salt quantity (% dsb) | Sedimentation (%) | Zeta potential (mV) | Viscosity 5 s−1 | Viscosity 40 s−1 |
|---|---|---|---|---|---|---|---|
| calcium chloride dihydrate | 1 | 3.84 | 1.45% | 24.9 | 0 | 0 | 0 |
| calcium gluconate monohydrate | 1 | 11.72 | 4.42% | 18.1 | 0 | 0 | 0 |
| dolomite | 0 | 4.82 | 1.82% | 5.1 | −38.77 | 66 | 50 |
| calcium lactate pentahydrate | 1 | 8.05 | 3.04% | 24.1 | 0 | 0 | 0 |
| calcium carbonate | 0 | 2.61 | 0.98% | 3 | −15.43 | 77 | 54 |
| calcium citrate tetrahydrate | 1 | 4.97 | 1.88% | 8.4 | −15.87 | 188 | 107 |
| calcium glycerophosphate | 1 | 5.49 | 2.07% | 0 | −22.8 | 17 | 16 |
| calcium phosphate | 1 | 4.49 | 1.69% | 0 | −14.17 | 1125 | 738 |
| tricalcium phosphate | 0 | 2.68 | 1.01% | 4 | −39.03 | 83 | 59 |
| calcium dihydrogen pyrophosphate | 1 | 5.65 | 2.13% | 0 | −15.2 | 18 | 14 |
| calcium sulfate | 1 | 4.50 | 1.70% | 0 | −22.53 | 20 | 17 |
| calcium acetate monohydrate | 1 | 4.61 | 1.74% | 0 | −20.3 | 20 | 17 |
| calcium propionate | 1 | 4.87 | 1.84% | 0 | −10.92 | 20 | 17 |

As can be seen above, only tricalcium phosphate can both be added to reach required calcium salt level, with no coagulation and a zeta potential of less than −30. Dolomite can also work but is not qualified salt for food recipes.

As indicated above, each magnesium salt was incorporated in the liquid food composition in order to obtain the same quantity of magnesium cation.

|  | Visual observation | Salt (g) | Salt quantity (% dsb) | Sedimentation (%) | Zeta potential (mV) | Viscosity 5 s−1 | Viscosity 40 s−1 |
|---|---|---|---|---|---|---|---|
| magnesium carbonate | 0 | 0.65 | 0.25% | 0 | −35.9 | 82 | 59 |
| magnesium chloride hexahydrate | 1 | 1.51 | 0.57% | 23.3 | −26.47 | 12 | 12 |
| trimagnesium phosphate | 1 | 1.00 | 0.38% | 3.6 | −35.47 | 301 | 144 |
| magnesium sulfate anhydrous | 1 | 0.89 | 0.34% | 27.9 | −28.97 | 13 | 13 |

As can be seen from above, only magnesium carbonate can be added to reach required magnesium salt level, with no coagulation and a zeta potential less than −30.

These results are especially surprising as magnesium carbonate and tricalcium phosphate are soluble salts: soluble divalent salts when dissolving are generally used in order to react with soluble proteins and make them coagulate.

Liquid food compositions comprising magnesium carbonate and tricalcium phosphate in quantities going respectively from 0.15% to 0.35% and from 0.4% to 1.2%, based on the dry weight of the composition, are manufactured and no sedimentation and coagulation occur either.

Other liquid foods comprising a combination of magnesium carbonate and tricalcium phosphates were tested in examples 3, 4, 5 and 6.

Example 2: Effect of Various Potassium Salts Addition

As indicated above, each potassium salt was incorporated in the liquid food composition in order to obtain the same quantity of potassium cation.

|  | Visual observation | Salt quantity (g) | Salt quantity (% dsb) | Sedimentation (%) | Zeta potential (mV) | Viscosity 5 s−1 | Viscosity 40 s−1 |
|---|---|---|---|---|---|---|---|
| potassium citrate monohydrate | 0 | 5.34 | 2.02% | 5.9 | −40.3 | 432 | 189 |
| potassium gluconate | 1 | 11.57 | 4.37% | 35.1 | −32.17 | 28 | 23 |
| potassium carbonate | 0 | 3.41 | 1.29% | 0.8 | −42.87 | 59 | 49 |
| potassium chloride | 1 | 3.68 | 1.39% | 29.6 | −37.1 | 29 | 22 |
| potassium hydrate | 0 | 2.77 | 1.05% | 1.4 | −43 | 72 | 56 |
| potassium dihydrogenophosphate | 1 | 6.72 | 2.54% | 29.6 | −29.2 | 15 | 14 |

-continued

|  | Visual observation | Salt quantity (g) | Salt quantity (% dsb) | Sedimentation (%) | Zeta potential (mV) | Viscosity 5 s−1 | Viscosity 40 s−1 |
|---|---|---|---|---|---|---|---|
| dipotassium hydrogenophosphate | 0 | 4.30 | 1.62% | 2.8 | −37.83 | 240 | 127 |
| tripotassium phosphate | 0 | 3.49 | 1.32% | 1.1 | −40.7 | 82 | 60 |
| potassium pyrophosphate | 0 | 4.08 | 1.54% | 1.4 | −42.4 | 70 | 47 |
| potassium tripolyphosphate | 0 | 4.43 | 1.67% | 1.2 | −39.63 | 105 | 75 |
| potassium lactate | 1 | 6.33 | 2.39% | 29.3 | −35.9 | 31 | 24 |
| potassium metaphosphate | 0 | 5.83 | 2.20% | 2 | −62.63 | 126 | 84 |
| potassium hydrogen tartrate | 1 | 9.29 | 3.51% | 20.3 | 0 | 0 | 0 |
| potassium sulfate | 1 | 4.30 | 1.62% | 26 | −32.43 | 29 | 24 |

As can be seen from above, only potassium carbonate, tripotassium phosphate, potassium hydrate, potassium pyrophosphate, potassium tripolyphosphate and potassium metaphosphate can be added to reach required potassium salt level, with no coagulation and a zeta potential less than −30.

Example 3: Combination of Calcium, Magnesium and Potassium Salt in a Final Mix In this example, beverages were produced with 0.57 g of magnesium carbonate and 1.55 g of tricalcium phosphate, the ingredients others than minerals being the same as in Table 1 of the examples above. In addition, the following amounts of potassium and sodium salts were added to obtain a full mineral recipe. These contents in the various cations are the ones generally observed in commercial liquid pea protein supplemented milks. Contents of various sodium and potassium salts are the ones indicated in the Table below.

|  |  | Zeta potential (mV) |
|---|---|---|
| potassium carbonate (2.00 g, 0.75% dsb) | trisodium citrate (0.76 g, 0.29% dsb) | −31.9 |
|  | sodium hydrate (0.31 g, 0.12% dsb) | −31.03 |
|  | trisodium phosphate (0.42 g, 0.16% dsb) | 0 |
|  | disodium phosphate (0.55 g, 0.21% dsb) | 0 |
|  | sodium carbonate (0.41 g, 0.15% dsb) | −28.57 |
|  | sodium tetrapolyphosphate (0.61 g, 0.23% dsb)) | −30.3 |
| potassium hydrate (1.63 g, 0.62% dsb) | trisodium citrate (0.76 g) | 0 |
|  | sodium hydrate (0.31 g) | 0 |
|  | trisodium phosphate (0.42 g) | 0 |
|  | disodium phosphate (0.55 g) | 0 |
|  | sodium carbonate (0.41 g) | −28.63 |
|  | sodium tetrapolyphosphate (0.61 g) | −31.1 |
| tripotassium phosphate (2.60 g, 0.98% dsb) | trisodium citrate (0.76 g) | −31.17 |
|  | sodium hydrate (0.31 g) | −28.37 |
|  | trisodium phosphate (0.42 g) | −27.57 |
|  | disodium phosphate (0.55 g) | −26.33 |
|  | sodium carbonate (0.41 g) | −28.97 |
|  | sodium tetrapolyphosphate (0.61 g) | −28.6 |
| potassium pyrophosphate (2.40 g, 0.91% dsb) | trisodium citrate (0.76 g) | −36.6 |
|  | sodium hydrate (0.31 g) | −35.17 |
|  | trisodium phosphate (0.42 g) | −38.97 |
|  | disodium phosphate (0.55 g) | −36.83 |
|  | sodium carbonate (0.41 g) | −38.4 |
|  | sodium tetrapolyphosphate (0.61 g) | −35.37 |
| potassium tripolyphosphate (2.60 g, 0.98% dsb) | trisodium citrate (0.76 g) | −33.07 |
|  | sodium hydrate (0.31 g) | −32.63 |
|  | trisodium phosphate (0.42 g) | −32.73 |
|  | disodium phosphate (0.55 g) | −38.13 |
|  | sodium carbonate (0.41 g) | −37.83 |
|  | sodium tetrapolyphosphate (0.61 g) | −35.73 |
| potassium metaphosphate (3.45 g, 1.30% dsb) | trisodium citrate (0.76 g) | −35.4 |
|  | sodium hydrate (0.31 g) | −48 |
|  | trisodium phosphate (0.42 g) | −36.8 |
|  | disodium phosphate (0.55 g) | −37.2 |
|  | sodium carbonate (0.41 g) | −38 |
|  | sodium tetrapolyphosphate (0.61 g) | −35.33 |

In the presence of sodium salt, only the three last potassium salts, which correspond to potassium pyrophosphate, potassium tripolyphosphate and potassium metaphosphate, can be added in combination to magnesium carbonate and tricalcium phosphate and lead to a good final results for all of sodium salts (level of salts for nutritional requirements, no coagulation, zeta potential below −30).

Liquid food compositions comprising the same contents of magnesium carbonate and tricalcium and further comprising phosphate potassium pyrophosphate, potassium tripolyphosphate or potassium metaphosphate in quantities going respectively from 0.7% to 2%, from 0.7% to 2% and from 1% to 2.5%, based on the dry weight of the composition, are manufactured and no sedimentation and coagulation occur either.

Example 4: Comparison of Pea Protein and Soy Protein as Protein Source

The same recipes (combination of salts of Table of Example 3) were reproduced with other pea proteins (Shuangta pea protein isolate instead of Roquette pea protein isolate) and soy proteins.

|  |  | Visual observation | Zeta potential (mV) |
|---|---|---|---|
| Magnesium carbonate Tricalcium phosphate Potassium metaphosphate Trisodium phosphate | Soy isolate | 1 | Unable to measure, heavy coagulation |
|  | Pea isolate | 0 | −33.65 mV |
| Magnesium carbonate Tricalcium phosphate Potassium pyrophosphate Trisodium phosphate | Soy isolate | 1 | Unable to measure, heavy coagulation |
|  | Pea isolate | 0 | −39.20 mV |

As exemplified above, the salt recipe works with various pea protein sources, but does not work with soy protein.

Example 5: Blends of Pea Proteins

Example 5A—Pea Globulin and Pea Albumin

The same recipe as example 4 was reproduced except that the pea protein was replaced with a protein blend consisting of 75% of pea globulin and 25% of pea albumin. The manufacturing of this blend is described by example in the example 2 of the patent application WO2019/068998.

|  | Visual observation | Zeta potential (mV) |
|---|---|---|
| Blend pea globulin and pea albumin | 0 | −38.80 mV |

As exemplified above, the salt recipe works perfectly well with a protein blend comprising 75% of pea globulin and 25% of pea albumin.

Example 5B—Pea and Cereal Proteins

For this example, the same proportions as example 4 recipe were used, except that the pea protein isolate was replaced with a blend of pea protein isolate (Roquette) with cereal protein. The mass ratio between pea protein isolate and cereal protein was 70:30. As a cereal protein, hydrolyzed wheat protein (NUTRALYS® W, Roquette) and rice protein (UNIRICE S80, Barentz) were used.

For this example, a different process was used:
Dry blend the powders (except both emulsifiers),
Heat the water at 50° C.,
Add the blend of powders into the water at 50° C.,
Disperse with a whisk then mix with a high shear mixer (Silverson) during 30 min at 50° C. (2500 RPM),
Place the oil and the emulsifiers in a separate mixing vessel,
Stir and heat to 60° C.,
After the 30 min of hydration, add the oil to the main batch using a high shear for 5 minutes (6500 rpm),
Heat treatment: put the sample (28 g) in Rapid Viscosity Analyzer, Perten RVA 4800 regular and controlled heating (under pressure) at 140° C. in 9 minutes, maintaining temperature during 5 sec, regular and controlled cooling at 50° C. in 9 minutes.

For both of the samples, no coagulation was observed at the end of the heat treatment, demonstrating that the composition of the invention can comprise other proteins such as cereal proteins.

Example 6: Pilot Scale Trials 2 batches were prepared in a mixer, using 2 different mineral mixes. Example 6A is a liquid food composition comprising Magnesium carbonate, Tricalcium phosphate, Potassium metaphosphate and Trisodium phosphate. Example 6B comprises Magnesium carbonate, Tricalcium phosphate, Potassium pyrophosphate and Trisodium phosphate. The relative proportions were the same as in the liquid food compositions of Example 3 and the quantities of each ingredient are chosen to manufacture, for each example, one batch of 7 litres of liquid food compositions. The process to manufacture one batch is the following:
Dry blend the powders (except both emulsifiers)
Heat the water at 50° C.,
Add the blend of powders into the water at 50° C., disperse with a whisk then mix with a high shear mixor (Silverson) for 30 min, 50° C., 2500 RPM.
Place the oil and the emulsifiers in a separate mixing vessel; stir and heat to 60° C.,
After the 30 min of hydration, add the oil to the main batch using a high shear for 5 minutes (6500 rpm),
Heat treating the liquid food composition using tubular exchanger at 142° C. during 5 sec (Powerpoint international),
Homogenization of the liquid food composition using a 2 stages homogenizer Upstream at 200 bars_2 stages (30% on the 2nd stage) (GEA Twin Panda 400 (NS2002H))
Cool it at 15° C. and store it at 4° C.

Homogenization step was conducted before the heat treatment (upstream) or after (downstream).

| Example | Zeta potential | Coagulation | d-10 (μm) | d-50 (μm) | d-90 (μm) | Taste |
|---|---|---|---|---|---|---|
| 6A upstream | −29 mV | No | 3.27 | 11.1 | 30.3 | Smooth, slightly viscous |
| 6A downstream | −32 mV | No | 0.3 | 0.9 | 10.5 | Smooth, not viscous |
| 6B upstream | −37 mV | No | 0.4 | 4.6 | 15.1 | Smooth, slightly viscous |
| 6B downstream | −36 mV | No | 0.3 | 0.6 | 10.0 | Smooth, not viscous |

These examples demonstrate that the use of the salts of the invention allow to obtain stable liquid compositions. The particle sizes also demonstrate that downstream homogenization gives a less viscous liquid beverage but, in both cases, the liquid food composition presents a pleasant texture in mouth.

Example 7: Fava Bean Protein

For example 7A, example 5B was repeated except that fava bean protein isolate was used instead of pea protein blend. For example 7B, example 7A was repeated except that Potassium pyrophosphate was replaced by potassium hydrate. The manufacture of this fava bean protein isolate is described in example 2b of the patent application WO2020/193641. For both samples of examples 7A and 7B, no coagulation was observed at the end of the heat treatment, demonstrating that the composition of the invention work as well with fava bean protein isolate.

The invention claimed is:

1. A liquid food composition, comprising protein and minerals sources wherein the source of the protein is from pea and/or fava bean and the source of the minerals comprises magnesium carbonate and tricalcium phosphate.

2. The liquid food composition of claim 1, wherein the protein comprises pea globulins and/or fava bean globulins.

3. The liquid food composition of claim 2, wherein the source of the protein consists, based on the total content of protein, of at least 60% by weight of pea globulins and/or fava bean globulins and at most 40% by weight of another source of protein, preferably cereal proteins and/or pea albumins.

4. The liquid food composition of claim 3, wherein the source of protein consists, base on the total content of protein, of at least 75% weight of pea globulins and at most 25% by weight of another source of protein, in order to reach Protein Digestibility Corrected Amino Acid Score of 1.

5. The liquid food composition of claim 1, wherein amount of the magnesium carbonate in the composition is from 0.15% to 0.3-5% by weight based on the dry weight of the composition and/or amount of the tricalcium phosphate in the composition is from 0.4% to 1.2% by weight based on dry weight of the composition.

6. The liquid food composition of claim 1, wherein amount of the magnesium carbonate in the composition is from 0.20% to 0.30%, and/or wherein amount of the tricalcium phosphate in the composition is from 0.8% to 1.2%, by weight based on dry weight of the composition.

7. The liquid food composition of claim 1, further comprising a potassium source selected in the group consisting of potassium pyrophosphate, potassium tripolyphosphate and potassium metaphosphate.

8. The liquid food composition of claim 7, wherein amount of the potassium pyrophosphate in the composition is from 0.7% to 2% by weight based on dry weight of the composition or amount of the potassium tripolyphosphate in the composition is from 0.7% to 2% by weight based on dry weight of the composition; or amount of the potassium metaphosphate in the composition is from 1% to 2-5% by weight based on dry weight of the composition.

9. The liquid food composition of claim 7, wherein amount of the potassium pyrophosphate in the composition is from 1% to 2%, by weight based on the dry weight of the composition and/or amount of the potassium tripolyphosphate in the composition is from 1% to 2%, by weight based on the dry weight of the composition; and/or amount of the potassium metaphosphate in the composition is from 1.5% to 2.5%, by weight based on the dry weight of the composition.

10. The liquid food composition of claim 7, wherein amount of the magnesium carbonate in the composition is from 0.15% to 0.35% by weight based on the weight of the composition, amount of the tricalcium phosphate in the composition is from 0.4% to 1.0% by weight based on weight of the composition, and amount of the potassium pyrophosphate in the composition is from 0.7% to 1.2% by weight based on dry weight of the composition, and/or amount of the potassium tripolyphosphate in the composition is from 0.7% to 1.2% by weight based on dry weight of the composition; and/or amount of potassium metaphosphate in the composition is from 1% to 1-5% by weight based on dry weight of the composition.

11. The liquid food composition of claim 1, wherein zeta potential is below −30 mV.

12. The liquid food composition of claim 1, wherein the source of the protein is from the pea.

13. A process for preparing a liquid food composition, comprising mixing pea and/or fava bean proteins, magnesium carbonate and tricalcium phosphate.

14. The process according to claim 13, wherein the process involves mixing, on the one hand, an aqueous solution or suspension comprising pea and/or fava bean proteins with, on the other hand, an aqueous solution comprising magnesium carbonate and tricalcium phosphate.

15. The process according to claim 13, wherein it further comprises addition of one or more nutritional additives chosen from soluble fibers, sugar, vegetable oils, emulsifying agents, food dyes, preservatives or sweeteners.

16. The process according to claim 13, further comprising a step of homogenization at high pressure, preferably at a pressure of between 2 MPa and 800 MPa, for example between 2 MPa and 250 MPa, for example between 3 MPa and 100 MPa, in particular between 15 MPa and 50 MPa, and most particularly at approximately 20 MPa.

17. The process according to claim 13, further comprising a step of heating the composition for a period of time sufficient to inhibit the enzymes and any form of microorganisms.

18. The liquid food composition of claim 3, wherein the another source of protein is pea albumins.

19. The liquid food composition of claim 6, wherein the amount of the tricalcium phosphate in the composition is from 0.9% to 1.1%, by weight based on the dry weight of the composition.

20. The liquid food composition of claim 9, wherein the amount of the potassium pyrophosphate in the composition is from 1.25% to 1.75%, by weight based on the dry weight of the composition; and/or the amount of the potassium tripolyphosphate in the composition is from 1.25% to 1.75%, by weight based on the dry weight of the composition; and/or the amount of the potassium metaphosphate in the composition is from 1.75% to 2.25%, by weight based on the dry weight of the composition.

21. The liquid food composition of claim 11, wherein the zeta potential is between −35 mV and −45 mV.

* * * * *